United States Patent
Smith et al.

(10) Patent No.: US 11,551,827 B2
(45) Date of Patent: *Jan. 10, 2023

(54) PERFLUORINATED 1-ALKOXYPROPENES IN DIELECTRIC FLUIDS AND ELECTRICAL DEVICES

(71) Applicant: 3M INNOVATIVE PROPERTIES COMPANY, St. Paul, MN (US)

(72) Inventors: Sean M. Smith, Woodbury, MN (US); Michael G. Costello, Afton, MN (US); Klaus Hintzer, Kastl (DE); Markus E. Hirschberg, Mühldorf (DE); William M. Lamanna, Stillwater, MN (US); John G. Owens, Woodbury, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 276 days.

This patent is subject to a terminal disclaimer.

(21) Appl. No.: 15/733,209

(22) PCT Filed: Dec. 12, 2018

(86) PCT No.: PCT/IB2018/059946
§ 371 (c)(1),
(2) Date: Jun. 10, 2020

(87) PCT Pub. No.: WO2019/116264
PCT Pub. Date: Jun. 20, 2019

(65) Prior Publication Data
US 2020/0388412 A1    Dec. 10, 2020

Related U.S. Application Data

(60) Provisional application No. 62/598,294, filed on Dec. 13, 2017.

(51) Int. Cl.
C07C 43/17    (2006.01)
C07C 21/18    (2006.01)
(Continued)

(52) U.S. Cl.
CPC ............... H01B 3/24 (2013.01); C07C 21/18 (2013.01); C07C 43/17 (2013.01); H01H 33/56 (2013.01); H01H 2033/566 (2013.01)

(58) Field of Classification Search
None
See application file for complete search history.

(56) References Cited

U.S. PATENT DOCUMENTS

| | | |
|---|---|---|
| 3,184,533 A | 5/1965 | Eiseman, Jr. |
| 3,752,840 A | 8/1973 | Oxenrider |

(Continued)

FOREIGN PATENT DOCUMENTS

| | | |
|---|---|---|
| EP | 1325949 | 7/2003 |
| GB | 1242180 | 8/1971 |

(Continued)

OTHER PUBLICATIONS

Abe, "A New Route to Perfluorovinylamines by the Pyrolytic Reaction of an Alkali Metal Salt of Perfluoro (2-dialkylamino-propionic acids)", Chemistry Letters, 1988, vol. 17, No. 11, pp. 1887-1890.

(Continued)

*Primary Examiner* — Medhanit W Bahta
(74) *Attorney, Agent, or Firm* — Jeffrey M. Olofson (57) ABSTRACT

A dielectric fluid (i.e., dielectric composition) that includes a perfluorinated 1-alkoxypropene compound represented by the following general Formula (I): $R_fO-CF=CFCF_3$ wherein $R_f$ is $CF_3-$ or $CF_3CF_2-$. Such dielectric fluids may be useful in various electrical devices.

13 Claims, 1 Drawing Sheet

(51) Int. Cl.
  *H01B 3/24* (2006.01)
  *H01H 33/56* (2006.01)

(56) References Cited

U.S. PATENT DOCUMENTS

| | | | |
|---|---|---|---|
| 4,288,651 A | 9/1981 | Wootton | |
| 4,741,744 A | 5/1988 | Wu | |
| 4,782,148 A | 11/1988 | Abe | |
| 4,899,249 A | 2/1990 | Reilly | |
| 4,985,556 A | 1/1991 | Abe | |
| 5,962,390 A | 10/1999 | Flynn | |
| 7,736,537 B1 | 6/2010 | Zastrow | |
| 8,418,530 B1 | 4/2013 | Scaringe | |
| 9,837,801 B2 | 12/2017 | Kieffel | |
| 9,899,125 B2 | 2/2018 | Kieffel | |
| 10,643,764 B2 | 5/2020 | Biquez | |
| 2003/0209685 A1* | 11/2003 | Robin | C07C 43/123 |
| | | | 252/2 |
| 2009/0048424 A1 | 2/2009 | Watakabe | |
| 2011/0076572 A1* | 3/2011 | Amine | H01M 10/05 |
| | | | 429/328 |
| 2015/0083979 A1 | 3/2015 | Costello | |
| 2016/0312096 A1 | 10/2016 | Bulinski | |
| 2018/0040391 A1 | 2/2018 | Kieffel | |
| 2018/0358148 A1 | 12/2018 | Kieffel | |
| 2019/0156968 A1 | 5/2019 | Gautschi | |

FOREIGN PATENT DOCUMENTS

| | | |
|---|---|---|
| GB | 2070012 | 9/1981 |
| JP | S56-25133 | 3/1981 |
| JP | S56-55336 | 5/1981 |
| JP | S64-70445 | 3/1989 |
| JP | H05-325970 | 12/1993 |
| JP | H08-291299 | 11/1996 |
| JP | 2002-187863 | 7/2002 |
| WO | WO 1999-037598 | 7/1999 |
| WO | WO 2000-015588 | 3/2000 |
| WO | WO 2000-070289 | 11/2000 |
| WO | WO 2002-040102 | 5/2002 |
| WO | WO 2009-141053 | 11/2009 |
| WO | WO 2012-102915 | 8/2012 |
| WO | WO 2013-151741 | 10/2013 |
| WO | WO 2014-037566 | 3/2014 |
| WO | WO 2014-110329 | 7/2014 |
| WO | WO 2015-013155 | 1/2015 |
| WO | WO 2015-040069 | 3/2015 |
| WO | WO 2015-071303 | 5/2015 |
| WO | WO 2015-097143 | 7/2015 |
| WO | WO 2016-048808 | 3/2016 |
| WO | WO 2016-094113 | 6/2016 |
| WO | WO 2016-096129 | 6/2016 |
| WO | WO 2016-109203 | 7/2016 |
| WO | WO 2016-116637 | 7/2016 |
| WO | WO 2016-128571 | 8/2016 |
| WO | WO 2016-198390 | 12/2016 |
| WO | WO 2017-093259 | 6/2017 |
| WO | WO 2017-108141 | 6/2017 |
| WO | WO 2017-114862 | 7/2017 |
| WO | WO 2017-125536 | 7/2017 |
| WO | WO 2017-195070 | 11/2017 |
| WO | WO 2018-039096 | 3/2018 |
| WO | WO 2018-222384 | 12/2018 |
| WO | WO 2018-224908 | 12/2018 |
| WO | WO 2019-082053 | 5/2019 |
| WO | WO 2019-116260 | 6/2019 |
| WO | WO 2019-116264 | 6/2019 |

OTHER PUBLICATIONS

Abe, "An Alternative New Route to Perfluorovinylamines. Pyrolysis of an Alkali Metal Salt of Perfluoro (3-dialkylamino-propionic acids)", Chemistry Letters, 1989, vol. 18, No. 5, pp. 905-908.

Abe, "The Electrochemical Fluorination of Nitrogen-Containing Carboxylic Acids. Fluorination of Dimethylamino-Substituted Carboxylic Acid Derivatives", Journal of Fluorine Chemistry, 1990, vol. 48, pp. 257-279.

Abe, "The Electrochemical Fluorination of Nitrogen-Containing Carboxylic Acids. Fluorination of Methyl Esters of Cyclic Amino-Group Substituted Carboxylic Acids", Journal of Fluorine Chemistry, 1990, vol. 50, pp. 173-196.

Andersen, "Atmospheric Chemistry of (CF3)2CF-C°N: A Replacement Compound for the Most Potent Industrial Greenhouse Gas, SF6", Environmental Science & Technology, 2017, Vo. 51 No. 3, pp. 1321-1329.

Barlow, "Heterocyclic Polyfluoro-Compounds. Part 30. Perfluoroalkylation of trifluoro-1,2,4-triazine", Journal of the Chemical Society, Perkin Transactions 1: Organic and Bio-Organic Chemistry, 1980, pp. 2254-2257.

Barnes, "Photochemistry of halocarbon compounds. Part 4. Photochemical conversions of some fluorinated aza- and Diazacyclohexadienes", Journal of the Chemical Society, Perkin Transactions 1: Organic and Bio-Organic Chemistry, 1981, pp. 3289-3291.

Chambers, "Photochemical conversions of some fluorinated aza- and diazacyclohexadienes", Journal of the Chemical Society, Chemical Communications, 1978, No. 7, pp. 305-306.

Chambers, "Photochemistry of halocarbon compounds. Part 5. Photolysis of fluorinated 1,2,3-triazine derivatives", Journal of the Chemical Society, Perkin Transactions 1: Organic and Bio-Organic Chemistry, 1990, No. 4, pp. 975-981.

Chambers, "Photochemistry of halocarbon compounds. Part 6. Direct Observation of fluorinated azetes", Journal of the Chemical Society, Perkin Transactions 1: Organic and Bio-Organic Chemistry, 1990, No. 4, pp. 983-987.

Chambers, "Possible generation of a fluorinated azacyclobutadiene", Journal of the Chemical Society, Chemical Communications, 1976, No. 24, pp. 1005-1006.

Cheburkov, "Perfluoroalcohols", Journal of Fluorine Chemistry, Dec. 2002, vol. 118, No. 1-2, pp. 123-126.

Chepik, "Electrophilic Alkenylation of Fluoroolefins with Perfluoro(2-alkoxypropenes)", Bulletin of the Academy of Sciences of the USSR, Division of chemical science, Aug. 1991, vol. 40, pp. 1712-1714 (Translated from Izvestiya Akademii Nauk SSSR Seriya Khimicheskaya, No. 8, pp. 1926-1928).

Cherstov, "Sulfotrioxidation of perfluoroisopropyl alkenyl ethers", Bulletin of the Academy of Sciences of the USSR, Division of chemical science, Dec. 1982, vol. 31, pp. 2472-2473 (Translated from Izvestiya Akademii Nauk SSSR Seriya Khimicheskaya, No. 12, pp. 2796-2798).

Ellis, "Cleaning and Contamination of Electronics Components and Assemblies", Electrochemical Publications Limited, 1986, pp. 182-194.

Galimberti, "New catalytic alkylation of in situ generated perfluoroalkyloxy-anions and perfluoro-carbanions", Journal of Fluorine Chemistry, Dec. 2005, vol. 126, No. 11-12, pp. 1578-1586.

Jelier, "A Convenient Route to Tetraalkylammonium Perfluoroalkoxides from Hydrofluoroethers", Angewandte Chemie International Edition, Mar. 2015, vol. 54, No. 10, pp. 2945-2949.

McLinden, "A Thermodynamic Analysis of Refrigerants: Possibilities and Tradeoffs for Low-GWP Refrigerants", International Journal of Refrigeration, Feb. 2014, vol. 38, pp. 80-92.

OECD Test No. 436: "Acute Inhalation Toxicity—Acute Toxic Class Method", OECD Guideline for The Testing of Chemicals, Sep. 2009, 27 pages.

OPPTS 870.1100: "Acute Oral Toxicity" U.S. EPA Health Effects Test Guidelines, Dec. 2002, 37 pages.

Pinnock, "Radiative forcing of climate by hydrochlorofluorocarbons and hydrofluorocarbons", Journal of Geophysical Research: Atmospheres, Nov. 1995, vol. 100, No. D11, pp. 23227-23238.

Wlassics, "Perfluoro Allyl Fluorosulfate (FAFS): A Versatile Building Block for New Fluoroallylic Compounds", Molecules, Dec. 2011, vol. 16, No. 8, pp. 6512-6540.

International Search Report for PCT International Application No. PCT-IB2018-059941, dated Mar. 25, 2019, 5pages.

(56) References Cited

OTHER PUBLICATIONS

International Search Report for PCT International Application No. PCT-IB2018-059943, dated Mar. 27, 2019, 5pages.
International Search Report for PCT International Application No. PCT-IB2018-059946, dated Mar. 15, 2019, 4pages.

* cited by examiner

PERFLUORINATED 1-ALKOXYPROPENES IN DIELECTRIC FLUIDS AND ELECTRICAL DEVICES

CROSS REFERENCE TO RELATED APPLICATIONS

This application is a national stage filing under 35 U.S.C. 371 of PCT/IB2018/059946, filed Dec. 12, 2018, which claims the benefit of U.S. Provisional Application No. 62/598,294, filed Dec. 13, 2017, the disclosure of which is incorporated by reference in its/their entirety herein.

BACKGROUND

Dielectric gases are used in various electrical devices such as, for example, capacitors, transformers, electric cables or buses, circuit breakers, and switchgear. In such electrical devices, dielectric gases are often used in place of air as an electrical insulator due to their higher dielectric strength (DS). Such dielectric gases allow higher power densities as compared to air-filled electrical devices.

Sulfur hexafluoride ($SF_6$) has become the dominant captive dielectric gas in many electrical applications. $SF_6$ is advantageously nontoxic, nonflammable, easy to handle, has a useful operating temperature range, and has excellent dielectric and arc-interrupting properties. Within transformers, it also acts as a coolant. Blowers within the transformer often circulate the gas aiding in heat transfer from the windings. A concern, however, with $SF_6$ is its 3200-year atmospheric lifetime and global warming potential (GWP) of about 22,200 times the global warming potential of carbon dioxide.

As possible replacements, mixtures of $SF_6$ with nitrogen, helium, or high-pressure nitrogen have been suggested. Also identified are perfluorocarbon (PFC) gases that might be mixed with nitrogen or helium; however, PFC gases also have high GWP values so the possible reduction in environmental impact of such strategies is limited. Some other replacement mixtures suffer from release of free carbon during arcing, increased toxicity during or after arcing, and increased difficulty in gas handling during storage, recovery, and recycling. Thus, other replacements for such dielectric gases and mixtures thereof are desired.

SUMMARY

The present disclosure provides compositions including one or more perfluorinated 1-alkoxypropene compounds, and methods of using such compositions.

In some embodiments, a composition is provided that includes a perfluorinated 1-alkoxypropene compound represented by the following general Formula (I), which may be in a trans configuration or in a cis configuration:

$$R_fO-CF=CFCF_3 \qquad I$$

wherein  is $CF_3-$ or $CF_3CF_2-$. Such composition can be referred to as a dielectric composition or a dielectric fluid.

In some embodiments, such dielectric fluid may further include one or more secondary dielectric gases.

In some embodiments, an electrical device is provided that includes a dielectric fluid comprising a perfluorinated 1-alkoxypropene compound of Formula (I) and optionally one or more secondary dielectric gases. In some embodiments, such dielectric fluid is an insulator.

As used herein, the term "dielectric fluid" is inclusive of both liquid dielectrics and gaseous dielectrics. The physical state of the fluid, gaseous or liquid, is determined at the operating conditions of temperature and pressure of the electrical device in which it is used.

Herein, the term "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether they materially affect the activity or action of the listed elements. Any of the elements or combinations of elements that are recited in this specification in open-ended language (e.g., comprise and derivatives thereof), are considered to additionally be recited in closed-ended language (e.g., consist and derivatives thereof) and in partially closed-ended language (e.g., consist essentially, and derivatives thereof).

The words "preferred" and "preferably" refer to embodiments of the disclosure that may afford certain benefits, under certain circumstances. However, other claims may also be preferred, under the same or other circumstances. Furthermore, the recitation of one or more preferred claims does not imply that other claims are not useful and is not intended to exclude other claims from the scope of the disclosure.

In this application, terms such as "a," "an," and "the" are not intended to refer to only a singular entity but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all the listed elements or a combination of any two or more of the listed elements.

Also, herein, all numbers are assumed to be modified by the term "about" and in certain embodiments, preferably, by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also, herein, the recitations of numerical ranges by endpoints include all numbers subsumed within that range as well as the endpoints (e.g., 1 to 5 includes 1, 1.5, 2, 2.75, 3, 3.80, 4, 5, etc.).

As used herein, the term "room temperature" refers to a temperature of 20° C. to 25° C. or 22° C. to 25° C.

The term "in the range" or "within a range" (and similar statements) includes the endpoints of the stated range.

Groupings of alternative elements or embodiments disclosed herein are not to be construed as limitations. Each group member may be referred to and claimed individually or in any combination with other members of the group or other elements found therein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Reference throughout this specification to "one embodiment," "an embodiment," "certain embodiments," or "some embodiments," etc., means that a particular feature, configuration, composition, or characteristic described in connection with the embodiment is included in at least one embodiment of the invention. Thus, the appearances of such phrases in various places throughout this specification are not necessarily referring to the same embodiment of the invention. Furthermore, the particular features, configurations, compositions, or characteristics may be combined in any suitable manner in one or more embodiments.

The above summary of the present disclosure is not intended to describe each disclosed embodiment or every implementation of the present invention. The description that follows more particularly exemplifies illustrative embodiments. In several places throughout the application, guidance is provided through lists of examples, which examples may be used in various combinations. In each instance, the recited list serves only as a representative group and should not be interpreted as an exclusive list. Thus, the scope of the present disclosure should not be limited to the specific illustrative structures described herein, but rather extends at least to the structures described by the language of the claims, and the equivalents of those structures. Any of the elements that are positively recited in this specification as alternatives may be explicitly included in the claims or excluded from the claims, in any combination as desired. Although various theories and possible mechanisms may have been discussed herein, in no event should such discussions serve to limit the claimable subject matter.

DETAILED DESCRIPTION

Figure 1:
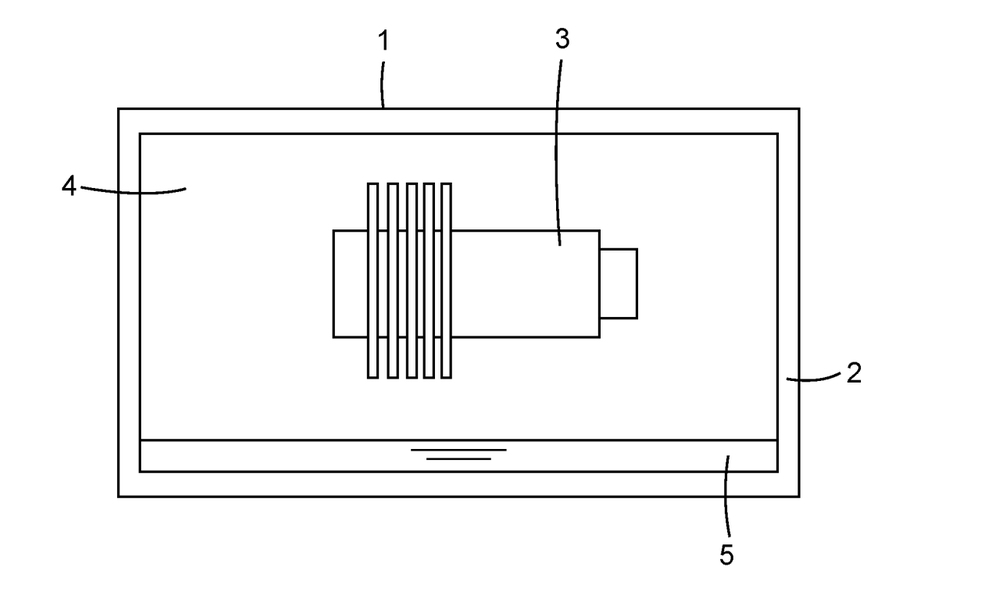
The FIGURE is an illustration of electrical hardware that includes a dielectric fluid comprising a perfluorinated 1-alkoxypropene compound in accordance with present disclosure.

In electrical devices such as capacitors, dielectric fluids are often used in place of air due to their low dielectric constant (K) and high dielectric strength (DS). Some capacitors of this type include alternate layers of metal foil conductors and solid dielectric sheets of paper or polymer film. Other capacitors are constructed by wrapping the metal foil conductor(s) and dielectric film(s) concentrically around a central core. This latter type of capacitor is referred to as a "film-wound" capacitor. Dielectric fluids are often used to impregnate dielectric films due to their low dielectric constant and high dielectric strength. Such dielectric fluids allow more energy to be stored within the capacitor (higher capacitance) as compared to air- or other gas-filled electrical devices.

The present disclosure, in illustrative embodiments, is directed to using a perfluorinated 1-alkoxypropene compound represented by the following general Formula (I), which may be in a trans configuration or in a cis configuration:

$R_fO—CF=CFCF_3$    I wherein $R_f$ is $CF_3—$ or $CF_3CF_2—$, as a dielectric fluid.

In some embodiments, the compounds of Formula (I) $CF_3—O—CF=CF—CF_3$ and $CF_3CF_2—O—CF=CF—CF_3$ are in the gas phase, liquid phase, or a combination thereof at the operating conditions of a device in which they are contained. The dielectric fluids of the present disclosure may be useful in electrical devices.

In certain embodiments, a mixture of compounds of Formula (I) is used. In certain embodiments of mixtures, at least a portion of the compounds is in the trans configuration and at least a portion of the compounds is in the cis configuration. In certain embodiments of $CF_3—O—CF=CF—CF_3$, at least a portion is in the cis configuration and at least a portion is in the trans configuration. In certain embodiments of $CF_3CF_2—O—CF=CF—CF_3$, at least a portion is in the cis configuration and at least a portion is in the trans configuration.

The perfluorinated 1-alkoxypropene compounds of Formula (I) can be prepared from reaction of a Lewis Acid with a perfluoroalkyl ether compound represented by the following general Formula (II):

wherein $R_f$ is as described for Formula (I). Examples of Lewis Acids include $TiF_4$, $ZrF_4$, $NbF_5$, $TaF_5$, $BF_3$, $SbF_5$, ACF (aluminum chlorofluoride), $SbCl_2F_3$, $SbCl_4F$, $HSbF_6$, $SbCl_5$, $AlCl_3$, and mixtures thereof. Exemplary conditions for such preparative reactions are presented in the Examples Section.

This disclosure further provides an electrical device that includes a dielectric fluid including a perfluorinated 1-alkoxypropene compound represented by Formula (I). In some embodiments, the present disclosure further provides a dielectric fluid comprising a mixture of one or more perfluorinated 1-alkoxypropene compounds represented by Formula (I) and one or more secondary dielectric gases.

The perfluorinated 1-alkoxypropene compounds represented by Formula (I) of the present disclosure advantageously have broad ranges of operating temperatures and pressures, are thermally and chemically stable, have higher dielectric strengths and heat transfer efficiencies than $SF_6$ at a given partial pressure, and have a lower global warming potential (GWP) than $SF_6$. Additionally, the perfluorinated 1-alkoxypropene compounds represented by Formula (I) of the present disclosure have toxicities surprisingly low. The perfluorinated 1-alkoxypropene compounds represented by Formula (I) generally have dielectric strengths of at least 50 kV/in (kilovolts per inch) at an operating pressure of 20 kPa (kilopascals) and at the operating temperature of an electrical device in which they are contained.

As used herein, global warming potential "GWP" is a relative measure of the warming potential of a compound based on the structure of the compound. The GWP of a compound, as defined by the Intergovernmental Panel on Climate Change (IPCC) in 1990 and updated in 2007, is calculated as the warming due to the release of 1 kilogram of a compound relative to the warming due to the release of 1 kilogram of $CO_2$ over a specified integration time horizon (ITH).

$$GWP_i(t') = \frac{\int_0^{ITH} a_i[C(t)]dt}{\int_0^{ITH} a_{CO_2}[C_{CO_2}(t)]dt} = \frac{\int_0^{ITH} a_i C_{oi} e^{-t/\tau} dt}{\int_0^{ITH} a_{CO_2}[C_{CO_2}(t)]dt}$$

In this equation a is the radiative forcing per unit mass increase of a compound in the atmosphere (the change in the flux of radiation through the atmosphere due to the IR absorbance of that compound), C is the atmospheric concentration of a compound, $\tau$ is the atmospheric lifetime of a compound, t is time, and i is the compound of interest.

The commonly accepted ITH is 100 years representing a compromise between short-term effects (20 years) and longer-term effects (500 years or longer). The concentration of an organic compound, i, in the atmosphere is assumed to follow pseudo first order kinetics (i.e., exponential decay). The concentration of $CO_2$ over that same time interval incorporates a more complex model for the exchange and removal of $CO_2$ from the atmosphere (the Bern carbon cycle model).

Because of degradation in the lower atmosphere, the perfluorinated 1-alkoxypropene compounds represented by Formula (I) have shorter lifetimes and would contribute less to global warming, as compared to $SF_6$. The GWP of perfluorinated 1-alkoxypropenes represented by Formula (I) can be less than 500, less than 250, less than 100, less than 50, or even less than 20. The lower GWP of perfluorinated 1-alkoxypropene compounds represented by Formula (I) in addition to the dielectric performance characteristics, as well as their relatively low toxicity, make them well suited for use as dielectric fluids.

Advantageously, the dielectric fluids of the present disclosure have a high electrical strength, also described as high breakdown voltage. Generally, "breakdown voltage," (at a specific frequency) refers to a voltage applied to a fluid that induces catastrophic failure of the fluid dielectric allowing electrical current to conduct through the fluid. Thus, the fluid dielectrics of the present disclosure can function under high voltages. The fluid dielectrics can also exhibit a low loss factor, that is, the amount of electrical energy that is lost as heat from an electrical device such as a capacitor.

In some embodiments, the perfluorinated 1-alkoxypropene compounds of Formula (I), when used as liquid dielectrics, have liquid phase ranges that encompass the operating temperature range of an electrical device in which either or both are used as a component.

In some embodiments, the perfluorinated 1-alkoxypropene compounds represented by Formula (I) have a gaseous phase range that encompasses the operating temperature range of an electrical device in which it is used as a dielectric component. For example, these compounds have a boiling point in a range of 0° C. to 35° C. Many electrical devices such as capacitors, transformers, circuit breakers, and gas insulated transmission lines may operate at temperatures of 30° C. and above.

The perfluorinated 1-alkoxypropene compounds represented by Formula (I) have a vapor pressure of at least 20 kPa at the operating temperature of an electrical device in which they are contained.

Further, the perfluorinated 1-alkoxypropene compounds represented by Formula (I) have a dielectric strength of at least 50 kV/inch at an operating pressure in the electric device of 20 kPa. More particularly, the perfluorinated 1-alkoxypropene compounds represented by Formula (I) have a dielectric strength of at least 80 kV/inch at the operating temperature and pressure of the device.

In some embodiments, the perfluorinated 1-alkoxypropene compounds represented by Formula (I) may be combined with one or more secondary dielectric gases with higher vapor pressure. In some embodiments, one or more secondary dielectric gases are used in an amount such that the vapor pressure is at least 70 kPa at 25° C., or at the operating temperature of the electrical device.

In some embodiments, the perfluorinated 1-alkoxypropene compounds represented by Formula (I) may be combined with one or more secondary dielectric gases with lower vapor pressure.

In some embodiments, the perfluorinated 1-alkoxypropene compounds represented by Formula (I) may be combined with one or more secondary dielectric gases which comprise 50 mole-% or more of the mixture.

These secondary dielectric gases typically have boiling points below 0° C., a zero ozone depletion potential, a global warming potential below that of $SF_6$ (about 22,200), and are chemically and thermally stable. They may be condensable or non-condensable gases. Combinations of such secondary dielectric gases may be used as desired.

In some embodiments, the secondary dielectric gases include one or more fluorinated organic compounds. Such fluorinated organic compounds include, for example: perfluoroalkanes such as those with 1 to 4 carbon atoms; fluorinated olefins such as $CF_3CH=CHCF_3$, $CF_3CH=CHCl$, $CF_3CF=CFCF_3$, $CF_3CF=CH_2$, $CF_3CH=CFH$, $CF_3CF=CFH$, $CF_3CH=CF_2$, or $HCF_2CF=CF_2$; fluorinated ketones such as $CF_3C(O)CF(CF_3)_2$, $CF_3CF_2C(O)CF(CF_3)_2$, $CF_3CF_2CF_2C(O)CF(CF_3)_2$, or $(CF_3)_2CFC(O)CF(CF_3)_2$; fluorinated nitriles such as $(CF_3)_2CFCN$; fluorinated nitroalkanes such as $CF_3CF_2NO_2$; fluorinated diones such as $CF_3C(O)C(O)CF_3$; and fluorinated oxiranes such as described in WO 2012/102915 (3M Company).

In some embodiments, the secondary dielectric gases include one or more gases selected from the group of nitrogen, carbon dioxide, nitrous oxide ($N_2O$), helium, argon, oxygen, and combinations thereof (e.g., air).

In some embodiments of dielectric fluids described herein, the perfluorinated 1-alkoxypropene compounds represented by Formula (I) may be combined with $SF_6$ such that the mixture of the dielectric fluid has a global warming potential below that of $SF_6$ alone.

In some embodiments, the ratio of the vapor pressure of a secondary dielectric gas to a perfluorinated 1-alkoxypropene compound represented by Formula (I) is at least 2.5:1, particularly at least 5:1, and more particularly at least about 10:1.

The perfluorinated 1-alkoxypropene compounds represented by Formula (I) may be useful in the gaseous phase for electrical insulation and for arc quenching and current interruption equipment used in the transmission and distribution of electrical energy.

The major types of electrical devices in which the gases of the present disclosure can be used include gas-insulated circuit breakers, current-interruption equipment including switchgear, gas-insulated transmission lines, gas-insulated transformers, and gas-insulated substations. Such gas-insulated equipment is a major component of power transmission and distribution systems all over the world.

In some embodiments, the present disclosure provides electrical devices, such as capacitors, including metal electrodes spaced from each other such that the gaseous dielectric fills the space between the electrodes. The interior space of the electrical device may also include a reservoir of one or more perfluorinated 1-alkoxypropene compounds of Formula (I) in liquid form. In certain embodiments, the reservoir includes one or more perfluorinated 1-alkoxypropene compounds of Formula (I) in liquid form in equilibrium with one or more perfluorinated 1-alkoxypropene compounds represented by Formula (I) in gaseous form. Thus, the reservoir may replenish any losses of the gaseous perfluorinated 1-alkoxypropene compounds of Formula (I).

For circuit breakers, the thermal conductivity and dielectric strength of such gases, along with the thermal and dielectric recovery (short time constant for increase in resistivity), may provide for high interruption capability. These properties enable the gas to make a rapid transition between the conducting (arc plasma) and the dielectric state of the arc, and also enable it to withstand the rise of the recovery voltage.

For gas-insulated transformers, the heat transfer performance and compatibility with current devices, in addition to the dielectric characteristics, make the dielectric fluids of the present disclosure a desirable medium for use in this type of electrical equipment.

The perfluorinated 1-alkoxypropene compounds represented by Formula (I) have distinct advantages over oil insulation, including having none of the fire safety problems or environmental compatibility issues, and having high reliability, little maintenance, long service life, low toxicity, ease of handling, and reduced equipment weight.

For gas-insulated transmission lines, the dielectric strength of the gaseous perfluorinated 1-alkoxypropene compounds of Formula (I) under industrial conditions may be significant, especially the behavior of the gaseous dielectric under metallic particle contamination, switching and lightning impulses, and fast transient electrical stresses. The gaseous perfluorinated 1-alkoxypropene compounds of Formula (I) may also have a high efficiency for transfer of heat from the conductor to the enclosure and may be stable for long periods (e.g., 40 years). These gas-insulated transmission lines may offer distinct advantages including, but not limited to, cost effectiveness, high-carrying capacity, low losses, availability at all voltage ratings, no fire risk, reliability, and a compact alternative to overhead high voltage transmission lines in congested areas that avoids public concerns with overhead transmission lines.

For gas-insulated substations, the entire substation (circuit breakers, disconnects, grounding switches, bus bar, transformers, etc., which are interconnected) may be insulated with the dielectric fluids of the present disclosure, and thus, all the above-mentioned properties of the dielectric gas are significant.

In some embodiments, the gaseous dielectric may be present in an electric device as a gas per se, or as a gas in equilibrium with the liquid. In these embodiments, the liquid phase may serve as a reservoir for additional dielectric gases.

The use of the perfluorinated 1-alkoxypropene compounds of Formula (I) as a dielectric fluid is illustrated in the generic electrical device of the figure. The figure illustrates a device including a tank or pressure vessel 2 containing electrical hardware 3, such as a switch, interrupter, or the windings of a transformer, and at least one gaseous perfluorinated 1-alkoxypropene compound of Formula (I). Optionally, a gaseous perfluorinated 1-alkoxypropene compound of Formula (I) is in equilibrium with a reservoir of a liquid perfluorinated 1-alkoxypropene compounds of Formula (I).

In another aspect, an electrical device is provided including, as an insulating material, a dielectric liquid including at least one perfluorinated 1-alkoxypropene compound of Formula (I). The dielectric fluids of the present disclosure may be useful in a number of other applications that use dielectric fluids. Examples of such other applications are described in U.S. Pat. No. 4,899,249 (Reilly et al.) and U.S. Pat. No. 3,184,533 (Eiseman, Jr.); and UK Patent No. 1 242 180 (Siemens).

EMBODIMENTS

Embodiment 1 is an electrical device comprising a dielectric fluid comprising a perfluorinated 1-alkoxypropene compound represented by the following general Formula (I):

$$R_fO\text{---}CF\text{=}CFCF_3 \qquad \qquad I$$

wherein $R_f$ is $CF_3$— or $CF_3CF_2$—.

Embodiment 2 is the electrical device of embodiment 1 further comprising a reservoir, wherein the reservoir comprises a perfluorinated 1-alkoxypropene compound of Formula (I) in liquid form.

Embodiment 3 is the electrical device of embodiment 2 wherein the reservoir further comprises a perfluorinated 1-alkoxypropene compound of Formula (I) in gaseous form in equilibrium with one or more perfluorinated 1-alkoxypropene compounds of Formula (I) in liquid form.

Embodiment 4 is the electrical device of any one of embodiments 1 to 3 wherein the electrical device is selected from the group consisting of gas-insulated circuit breakers, current-interruption equipment, gas-insulated transmission lines, gas-insulated transformers, and gas-insulated substations.

Embodiment 5 is the electrical device of any one of embodiments 1 to 4 wherein the dielectric fluid further comprises $SF_6$ such that the dielectric fluid has a global warming potential below that of $SF_6$ alone.

Embodiment 6 is the electrical device of any one of embodiments 1 to 5 wherein the dielectric fluid further comprises one or more secondary dielectric gases.

Embodiment 7 is the electrical device of embodiment 6 wherein the one or more secondary dielectric gases are used in an amount such that the vapor pressure is at least 70 kPa at 25° C.

Embodiment 8 is the electrical device of embodiment 6 or 7 wherein the one or more secondary dielectric gases have a boiling point below 0° C.

Embodiment 9 is the electrical device of any one of embodiments 6 to 8 wherein the one or more secondary dielectric gases comprise one or more fluorinated organic compounds.

Embodiment 10 is the electrical device of embodiment 9 wherein the fluorinated organic compounds comprise a perfluoroalkane, a fluorinated olefin, a fluorinated ketone, a fluorinated nitrile, a fluorinated nitroalkane, a fluorinated dione, a fluorinated oxirane, or combinations thereof.

Embodiment 11 is the electrical device of any one of embodiments 6 to 8 wherein the one or more secondary dielectric gases are selected from nitrogen, carbon dioxide, nitrous oxide, helium, argon, oxygen, and combinations thereof (e.g., air).

Embodiment 12 is the electrical device of any one of embodiments 6 to 11 wherein the ratio of the vapor pressure of a secondary dielectric gas to a perfluorinated 1-alkoxypropene compound of Formula (I) is at least 2.5:1 (at least 5:1, or at least about 10:1).

Embodiment 13 is the electrical device of any one of the previous embodiments wherein the compound of Formula (I) is in a trans configuration, a cis configuration, or a mixture thereof.

Embodiment 14 is the electrical device of embodiment 13 comprising a mixture of compounds of Formula (I), wherein at least a portion is in the trans configuration and at least a portion is in the cis configuration.

Embodiment 15 is the electrical device of any one of the previous embodiments wherein the compound of Formula (I) has a GWP of less than 500 (less than 250, less than 100, less than 50, or even less than 20).

Embodiment 16 is the electrical device of any one of the previous embodiments wherein the compound of Formula (I) has a boiling point in a range of 0° C. to 35° C.

Embodiment 17 is the electrical device of any one of embodiments 1 to 16 wherein the compound of Formula (I) is $CF_3$—O—CF=CF—$CF_3$.

Embodiment 18 is the electrical device of any one of embodiments 1 to 16 wherein the compound of Formula (I) is $CF_3CF_2$—O—CF=CF—$CF_3$.

Embodiment 19 is a dielectric fluid comprising: a perfluorinated 1-alkoxypropene compound represented by the following Formula (I):

$$R_fO\text{---}CF\text{=}CFCF_3 \qquad I$$

wherein $R_f$ is $CF_3$— or $CF_3CF_2$—; and one or more secondary dielectric gases.

Embodiment 20 is the dielectric fluid of embodiment 19 wherein the one or more secondary dielectric gases are used in an amount such that the vapor pressure is at least 70 kPa at 25° C.

Embodiment 21 is the dielectric fluid of embodiment 19 or 20 wherein the one or more secondary dielectric gases have a boiling point below 0° C.

Embodiment 22 is the dielectric fluid of any one of embodiments 19 to 21 wherein the one or more secondary dielectric gases comprise one or more fluorinated organic compounds.

Embodiment 23 is the dielectric fluid of embodiment 22 wherein the fluorinated organic compounds comprise a perfluoroalkane, a fluorinated olefin, a fluorinated ketone, a fluorinated oxirane, or combinations thereof.

Embodiment 24 is the dielectric fluid of any one of embodiments 19 to 21 wherein the one or more secondary dielectric gases are selected from nitrogen, carbon dioxide, nitrous oxide, helium, argon, oxygen, and combinations thereof (e.g., air).

Embodiment 25 is the dielectric fluid of any one of embodiments 19 to 24 wherein the ratio of the vapor pressure of a secondary dielectric gas to a perfluorinated 1-alkoxypropene compound of Formula (I) is at least 2.5:1 (at least 5:1, or at least about 10:1).

Embodiment 26 is the dielectric fluid of any one of embodiments 19 to 25 wherein the compound of Formula (I) is in a trans configuration, a cis configuration, or a mixture thereof.

Embodiment 27 is the dielectric fluid of embodiment 26 comprising a mixture of compounds of Formula (I), wherein at least a portion is in the trans configuration and at least a portion is in the cis configuration.

Embodiment 28 is the dielectric fluid of any one of embodiments 19 to 27 wherein the compound of Formula (I) has a GWP of less than 500 (less than 250, less than 100, less than 50, or even less than 20).

Embodiment 29 is the dielectric fluid of any one of embodiments 19 to 28 wherein the compound of Formula (I) has a boiling point in a range of 0° C. to 35° C.

Embodiment 30 is the dielectric fluid of any one of embodiments 19 to 29 wherein the compound of Formula (I) is $CF_3$—O—CF=CF—$CF_3$.

Embodiment 31 is the dielectric fluid of any one of embodiments 19 to 29 wherein the compound of Formula (I) is $CF_3CF_2$—O—CF=CF—$CF_3$.

Embodiment 32 is dielectric fluid of any one of embodiments 19 to 29 wherein the perfluorinated 1-alkoxypropene compounds represented by Formula (I) is combined with one or more secondary dielectric gases with a lower vapor pressure.

Embodiment 33 is the dielectric fluid of any one of the embodiments 19 to 29 wherein the one or more secondary dielectric gases comprise 50 mole-% or more of the fluid.

EXAMPLES

Objects and advantages of this disclosure are further illustrated by the following examples, but the particular materials and amounts thereof recited in these examples, as well as other conditions and details, should not be construed to unduly limit this disclosure. Unless otherwise noted, all parts, percentages, ratios, etc. in the examples and the rest of the specification are by weight, and all reagents used in the examples were obtained, or are available, from general chemical suppliers such as, for example, Sigma-Aldrich, Saint Louis, Mo., or may be synthesized by conventional methods. The following abbreviations are used in this section: mL=milliliters, h=hours, g=grams, mmol=millimoles, ° C.=degrees Celsius, mm=millimeters, NMR=nuclear magnetic resonance, GC-MS=gas chromatography-mass spectrometry, mm/Hg=millimeters of mercury, kPa=kilopascal, kV=kilovolt. Abbreviations for materials used in this section, as well as descriptions of the materials, are provided in Table 1.

TABLE 1

Glossary of Materials

| Material | Details |
|---|---|
| MA-1 | 1,1,2,3,3-pentafluoro-3-(perfluoromethoxy)prop-1-ene, can be prepared by methods described previously; See *Molecules* 2011, 16, 6512-6540 |
| MA-2 | 1,1,2,3,3-pentafluoro-3-(perfluoroethoxy)prop-1-ene, can be prepared by methods described previously; See *Molecules* 2011, 16, 6512-6540 |
| $AlCl_3$ | Aluminum(III) chloride, commercially available from Sigma-Aldrich Corp., Saint Louis, MO, USA |
| HFP (CE-1) | Hexafluoropropene, commercially available from SynQuest Laboratories, Alachua, FL, USA |
| $SF_6$(CE-2) | Sulfur hexafluoride, commercially available from SynQuest Laboratories, Alachua, FL, USA |
| Perfluorocyclopropane (CE-3) | Commercially available from SynQuest Laboratories, Alachua, FL, USA |
| Celite | Commercially available from Sigma-Aldrich Corp., Saint Louis, MO, USA |

Preparatory Example 1 (PE-1): Selective Preparation of 1,2,3,3,3-Pentafluoro-1-(Perfluoroethoxy) Prop-1-Ene (MP-2) Via $AlCl_3$-Catalyzed Isomerization of 1,1,2,3,3-Pentafluoro-3-(Perfluoroethoxy) Prop-1-Ene (MA-2)

A 40-mL vial equipped with a magnetic stir bar was charged with $AlCl_3$ (1.1 g, 8.2 mmol) and MA-2 (20.0 g, 75.2 mmol). The vial was capped and stirred at 50° C. for 16 h. The resultant reaction mixture was filtered over a pad of celite and the filtrate was analyzed by GC-FID which indicated greater than 99% conversion of the MA-2 starting material. The resultant product mixture was then purified by concentric tube distillation (33° C., 740 mm/Hg (98.7 kPa)) to afford the desired MP-2 (17.1 g, 86% isolated yield) as a colorless liquid. The structure was confirmed by GC-MS and $^{19}$F NMR analyses to be that of the desired compound.

Preparatory Example 2 (PE-2): Selective Preparation of 1,2,3,3,3-Pentafluoro-1-(Perfluoromethoxy) Prop-1-Ene (MP-1) Via AlCl$_3$-Catalyzed Isomerization of 1,1,2,3,3-Pentafluoro-3-(Perfluoromethoxy) Prop-1-Ene (MA-1)

A 600-mL stainless steel reactor equipped with an overhead stirrer was charged with AlCl$_3$ (2.3 g, 17 mmol). The reaction vessel was sealed and evacuated under reduced pressure followed by the addition of MA-1 (96 g, 444 mmol) followed by an overnight stir at 50° C. The headspace was then vented and condensed into a stainless steel cylinder submerged in a dry ice/acetone bath (−78° C.). Concentric tube distillation afforded MP-1 (boiling point less than 10° C., 79.3 g, 83% isolated yield). The structure was confirmed by GC-MS to be that of the desired compound.

Examples 1 and 2 (EX-1 and EX-2) and Counter Examples 1, 2, and 3 (CE-1, CE-2, and CE-3): Dielectric Breakdown Voltage Measurements The gaseous dielectric breakdown voltages of PE-1, PE-2, CE-1, CE-2, and CE-3 were measured experimentally using a Hipotronics OC60D-A dielectric strength tester (available from Hipotronics, Brewster, N.Y., USA), which was modified to allow measurements on low pressure gases. The electrode configuration consisted of two copper electrodes separated by a 0.1 inch (2.5 mm) gap housed in a gas tight PFTE (polytetrafluoroethylene) test chamber. The test chamber was first evacuated and then PE-1, PE-2, CE-1, CE-2, or CE-3 was charged to full vapor pressure and evacuated to the measured pressures indicated in Tables 2 and 3. The dielectric breakdown voltage (measured in kV) was measured after each evacuation to determine the dielectric strength and the results are summarized in Tables 2 and 3.

TABLE 2

Dielectric Breakdown Voltage of PE-1, PE-2, and CE-1

| | Dielectric breakdown voltage (kV) | | |
|---|---|---|---|
| Pressure (kPa) | PE-1 (EX-1) | PE-2 (EX-2) | CE-1 |
| 20 | 8.7 | 8.8 | 8.8 |
| 40 | 13.5 | 10.9 | 9.8 |
| 60 | 18.7 | 15.6 | 11.5 |
| 80 | N/M | 19.5 | 13.9 |
| 100 | N/M | 22.7 | 16.3 |
| 120 | N/M | 25.7 | 18.4 |
| 140 | N/M | 28.9 | 20.1 |

N/M = Not measurable due to vapor pressure

TABLE 3

Dielectric Breakdown Voltage of CE-2 and CE-3

| | Dielectric breakdown voltage (kV) | |
|---|---|---|
| Pressure (kPa) | CE-2 | CE-3 |
| 13.9 | 4.6 | 4.6 |
| 27.6 | 5.4 | 6.4 |
| 41.4 | 7.8 | 8.0 |
| 55.2 | 9.5 | 9.5 |
| 69.0 | 10.9 | 10.6 |
| 82.8 | 12.5 | 12.0 |
| 110 | 15.3 | 14.7 |
| 124 | 16.7 | 16.0 |
| 139 | 18.0 | 17.1 |

The dielectric breakdown voltage values in Tables 2 and 3 show that PE-1 and PE-2 are excellent electrical insulators and interrupters. Surprisingly, the dielectric breakdown voltages of PE-1 and PE-2 indicate that they can outperform related perfluoroolefins (HFP, CE-1), widely used SF$_6$ (CE-2), and perfluorocarbons (perfluorocyclopropane, CE-3).

The complete disclosures of the patents, patent documents, and publications cited herein are incorporated by reference in their entirety as if each were individually incorporated. To the extent that there is any conflict or discrepancy between this specification as written and the disclosure in any document that is incorporated by reference herein, this specification as written will control. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:

1. An electrical device comprising a dielectric fluid comprising a perfluorinated 1-alkoxypropene compound represented by the following general Formula (I):

$$R_fO\text{—}CF\text{=}CFCF_3 \qquad\qquad I$$

wherein $R_f$ is $CF_3$— or $CF_3CF_2$—.

2. The electrical device of claim 1 further comprising a reservoir, wherein the reservoir contains an amount of the dielectric fluid in liquid form.

3. The electrical device of claim 1 wherein the electrical device is selected from the group consisting of gas-insulated circuit breakers, current-interruption equipment, gas-insulated transmission lines, gas-insulated transformers, and gas-insulated substations.

4. The electrical device of claim 1 further comprising one or more secondary dielectric gases.

5. The electrical device of claim 4 wherein one or more secondary dielectric gases are selected from nitrogen, carbon dioxide, nitrous oxide, helium, argon, oxygen, and combinations thereof.

6. The electrical device of claim 4 wherein one or more secondary dielectric gases are selected from a perfluoroalkane, a fluorinated olefin, a fluorinated ketone, a fluorinated oxirane, a fluorinated nitrile, a fluorinated nitroalkane, a fluorinated dione, and combinations thereof.

7. The electrical device of claim 1 wherein the compound of Formula (I) is in a trans configuration, a cis configuration, or a mixture thereof.

8. The electrical device of claim 1 wherein the compound of Formula (I) is $$CF_3-O-CF=CF-CF_3.$$

9. The electrical device of claim 1 wherein the compound of Formula (I) is $CF_3CF_2-O-CF=CF-CF_3$.

10. A dielectric fluid comprising:
a perfluorinated 1-alkoxypropene compound represented by the following Formula (I):

$$R_fO-CF=CFCF_3 \qquad I$$

wherein $R_f$ is $CF_3-$ or $CF_3CF_2-$; and
one or more secondary dielectric gases, wherein the one or more secondary dielectric gases are selected from a perfluoroalkane, a fluorinated olefin, a fluorinated ketone, a fluorinated oxirane, a fluorinated nitrile, a fluorinated nitroalkane, a fluorinated dione, and combinations thereof.

11. The dielectric fluid of claim 10 wherein the one or more secondary dielectric gases are used in an amount such that the vapor pressure is at least 70 kPa at 25° C.

12. The dielectric fluid of claim 10 wherein a ratio of the vapor pressure of a secondary dielectric gas to a perfluorinated 1-alkoxypropene compound represented by Formula (I) is at least 2.5:1.

13. The dielectric fluid of claim 10 wherein the compound of Formula (I) is in a trans configuration, a cis configuration, or a mixture thereof.

* * * * *